United States Patent
Sato (10) Patent No.: US 9,298,351 B2
(45) Date of Patent: Mar. 29, 2016

(54) INSPECTION IMAGE DISPLAY APPARATUS, INSPECTION IMAGE DISPLAY METHOD AND STORAGE MEDIUM

(75) Inventor: Saichi Sato, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 659 days.

(21) Appl. No.: 13/554,590

(22) Filed: Jul. 20, 2012

(65) Prior Publication Data

US 2013/0033519 A1 Feb. 7, 2013

Related U.S. Application Data

(60) Provisional application No. 61/514,546, filed on Aug. 3, 2011.

(51) Int. Cl.
| | |
|---|---|
| *G06F 3/048* | (2013.01) |
| *G06F 17/30* | (2006.01) |
| *A61B 1/005* | (2006.01) |
| *G06F 3/0482* | (2013.01) |
| *A61B 1/00* | (2006.01) |

(52) U.S. Cl.
CPC .......... *G06F 3/0482* (2013.01); *A61B 1/00045* (2013.01); *G06F 17/30126* (2013.01); *G06F 17/30274* (2013.01)

(58) Field of Classification Search
CPC ............... G06F 17/30126; G06F 17/30274; A61B 1/00045
See application file for complete search history.

(56) References Cited

U.S. PATENT DOCUMENTS

| | | | |
|---|---|---|---|
| 2008/0129757 A1* | 6/2008 | Tanaka et al. | 345/660 |
| 2009/0037433 A1* | 2/2009 | Nakamura et al. | 707/10 |
| 2009/0303316 A1* | 12/2009 | Iwasaki et al. | 348/65 |

FOREIGN PATENT DOCUMENTS

| | | | |
|---|---|---|---|
| JP | 2003-009057 A | 1/2003 |
| JP | 2003-108976 A | 4/2003 |

OTHER PUBLICATIONS

Windows Vista Icons, Windows Dev Center—Desktop, downloaded on Jan. 16, 2015 from: http://msdn.microsoft.com/en-us/library/windows/desktop/dn742485(v=vs.85).aspx, pp. 1-10.*
Google Web Search Results for "Windows VISTA release date", search performed on and printed on Jan. 18, 2015, pp. 1-2.*

* cited by examiner

*Primary Examiner* — Jeffery A Brier
(74) *Attorney, Agent, or Firm* — Holtz, Holtz & Volek PC (57) ABSTRACT

A display switch section switches a display mode at a time of displaying inspection images stored in a storage device in which folders including a hierarchical structure are created by selecting the display mode from a predetermined display mode and a list display mode. A folder selecting section selects one folder to be an origin of list display when the list display mode is selected and a control section causes, in a list display region, each inspection image stored in each folder belonging to a folder group with the one folder as the origin to be list-displayed and causes to be displayed, in addition in the list display region, information which makes a folder in which a file of the inspection image is present and a folder in which the file of the inspection image is not present visually identifiable, in each folder belonging to the folder group.

20 Claims, 11 Drawing Sheets

INSPECTION IMAGE DISPLAY APPARATUS, INSPECTION IMAGE DISPLAY METHOD AND STORAGE MEDIUM

BACKGROUND OF THE INVENTION

1. Field of the Invention

The present invention relates to an inspection image display apparatus, an inspection image display method and a storage medium.

2. Description of the Related Art

Conventionally, endoscope apparatuses have been widely used in industrial fields and medical fields. An endoscope apparatus has an insertion portion having an image pickup unit provided at a distal end portion, and a user who is an inspector brings the distal end portion of the insertion portion close to an object, causes an image which is picked up by the image pickup unit at the distal end portion of the insertion portion to be displayed on a monitor, and can cause the image to be stored in a storage device in accordance with necessity. For example, the user can connect a storage device such as a USB memory to a main body and can store an endoscopic image in the storage device.

In a conventional endoscope apparatus, as disclosed in Japanese Patent Application Laid-Open Publication No. 2003-9057, a DCIM directory is automatically created in a root directory in the storage device in accordance with a DCF standard, and endoscopic images are automatically stored under the directory.

Further, Japanese Patent Application Laid-Open Publication No. 2003-108976 discloses an art of list-displaying all images in a selected folder including images in sub folders in a same screen in an image management system which manages images in a unit of a folder.

SUMMARY OF THE INVENTION

An inspection image display apparatus of one aspect of the present invention has a display switch section configured to switch a display mode at a time of displaying a plurality of inspection images stored in a storage device in which a plurality of folders including a hierarchical structure are created by selecting the display mode from any one of a predetermined display mode and a list display mode, a folder selecting section configured to select one folder to be an origin of list display from the plurality of folders when the list display mode is selected in the display switch section, and a control section that causes, in a list display region, each inspection image stored in each folder belonging to a folder group with the one folder as the origin to be list-displayed and causes to be displayed, in addition in the list display region, information which makes a folder in which a file of the inspection image is present and a folder in which the file of the inspection image is not present visually identifiable, in each folder belonging to the folder group, when the list display mode is selected in the display switch section.

DETAILED DESCRIPTION OF THE PREFERRED EMBODIMENT

Hereinafter, an embodiment of the present invention will be described with reference to the drawings. FIGS. 1 to 11 relate to the embodiment of the present invention.

Figure 1:
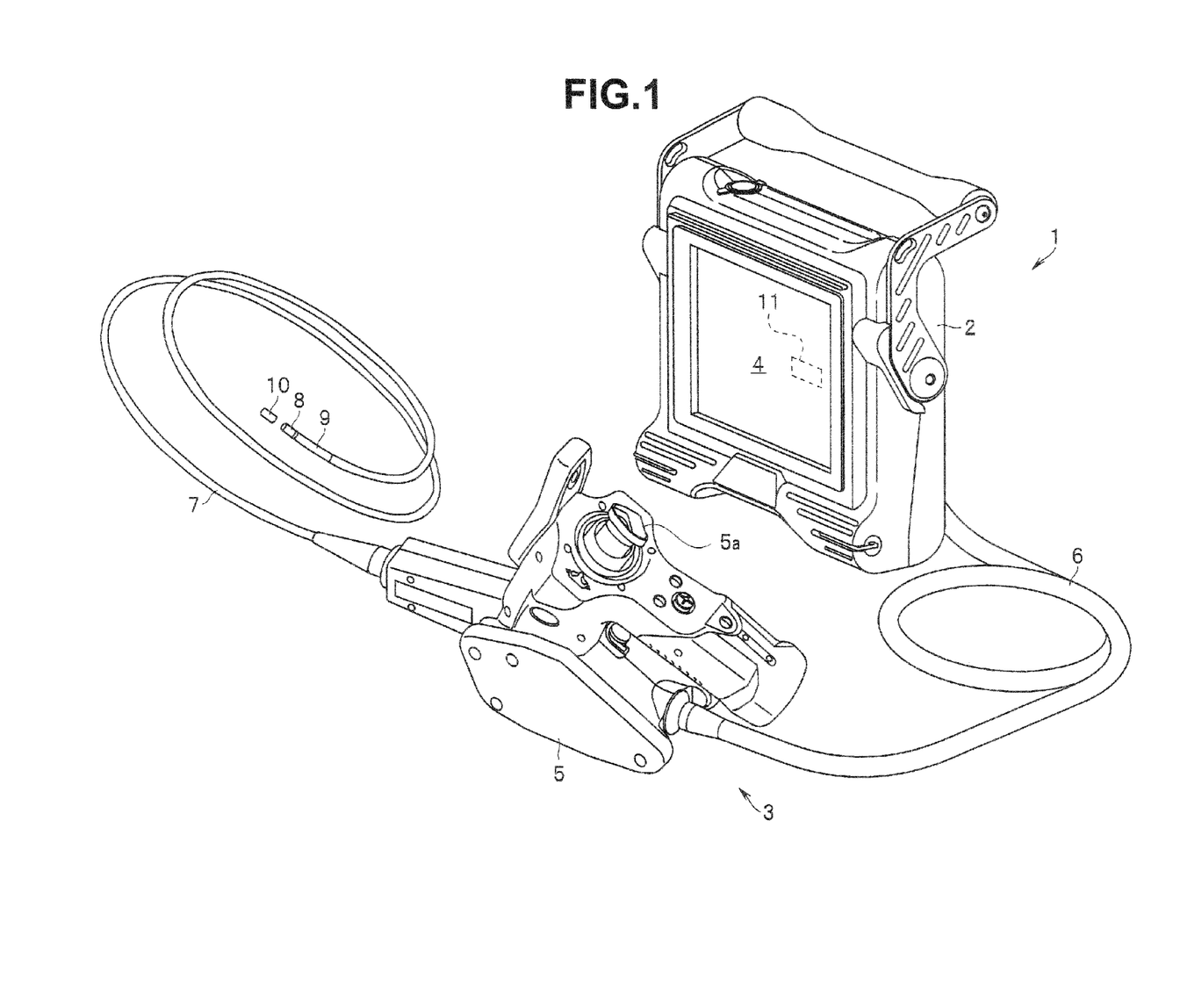
FIG. 1 is an external configuration view of an endoscope apparatus according to an embodiment of the present invention.

First, based on FIG. 1, a configuration of an endoscope apparatus according to the present embodiment will be described. FIG. 1 is an external configuration view of the endoscope apparatus according to the present embodiment.

Figure 2:
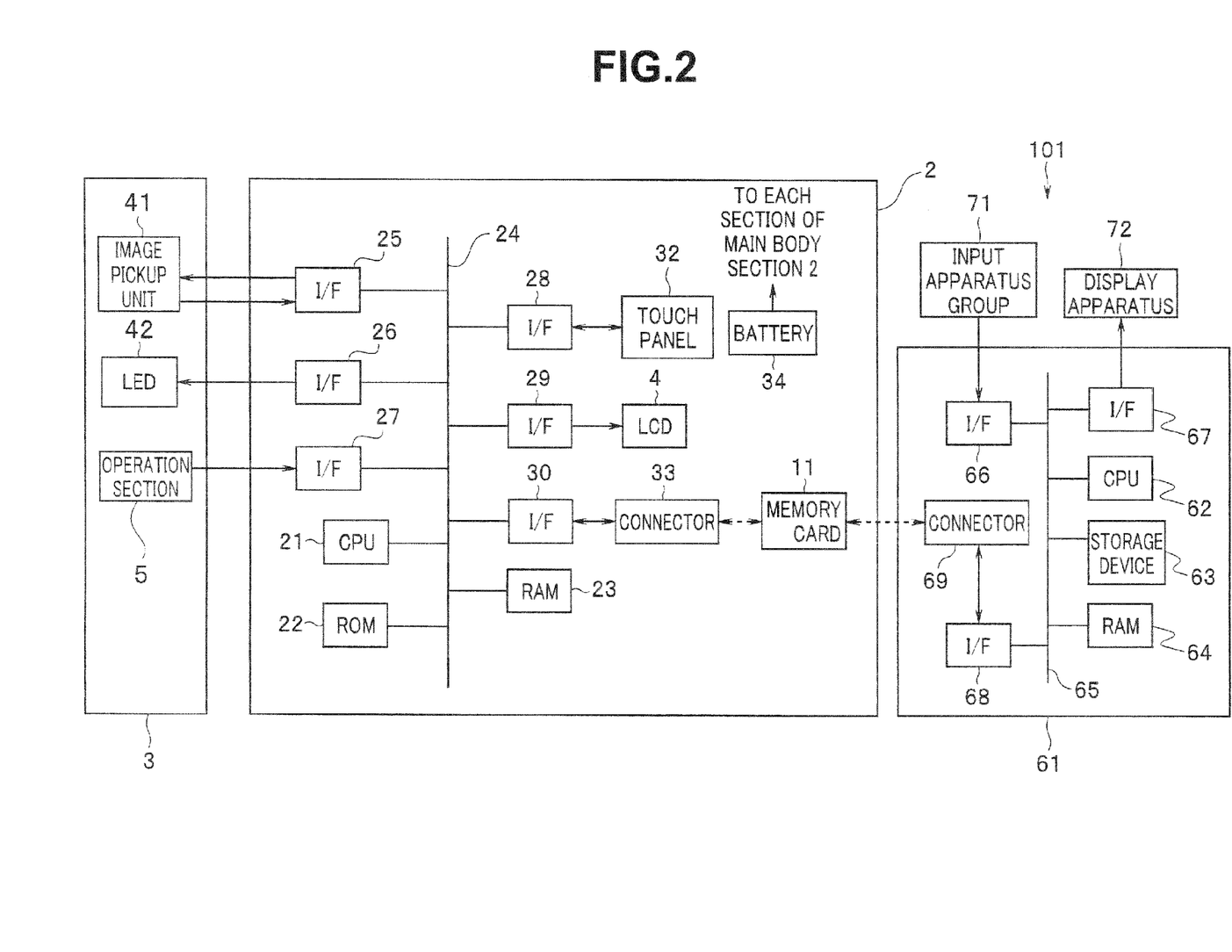
FIG. 2 is a block diagram for explaining an internal configuration of a main body section of the endoscope apparatus, and an internal configuration of a main body section of a personal computer.

As shown in FIG. 1, an endoscope apparatus 1 is configured to include a main body section 2 which is a main unit, and a scope unit 3 which is connected to the main body section 2. The main body section 2 has a liquid crystal display (hereinafter, abbreviated as an LCD) 4 as a display apparatus in which an endoscopic image, an operation menu and the like are displayed. As will be described later, the LCD 4 may be provided with a touch panel (FIG. 2). The scope unit 3 has an operation section 5, a universal cable 6 which is a connection cable for connecting the operation section 5 to the main body section 2, and an insertion portion 7 which includes a flexible insertion tube. The scope unit 3 is detachable from the main body section 2. An image pickup unit (FIG. 2) which will be described later is contained in a distal end portion 8 of the insertion portion 7. The image pickup unit is configured by an image pickup device, for example, a CCD sensor, a CMOS sensor or the like, and an image pickup optical system such as a lens which is disposed at an image pickup surface side of the image pickup device. A bending portion 9 is provided at a proximal end side of the distal end portion 8. An optical adapter 10 is configured to be attachable to the distal end portion 8. The operation section 5 is provided with various operation buttons such as a freeze button, a storage instruction button (hereinafter, a REC button), and an up, down, left and right (U/D/L/R) direction bending button.

A user can perform image pickup of an object, still image storage and the like by operating the various operation buttons of the operation section 5. Further, the user can select a storage destination folder by performing an operation of tilting a joystick 5a provided at the operation section 5 in any one of up, down, left and right directions, when the user performs change of the storage destination folder for an endoscopic image, which will be described later. Further, in a case of a configuration in which a touch panel is provided at the LCD 4, the user can give instructions of various operations of the endoscope apparatus 1 by operating the touch panel.

Image data of the endoscopic image which is picked up and obtained is stored in a memory card 11 as inspection data of an inspection target. The memory card 11 is detachable with respect to both the main body section 2 of the endoscope apparatus 1, and a main body section 61 of a personal computer (hereinafter, called PC) 101 which will be described later.

The user can bring the distal end portion 8 of the insertion portion 7 close to a site to be inspected of an inspection target, photograph the site to be inspected, obtain an endoscopic image, and display the endoscopic image on the LCD 4. Further, as will be described later, the user can change the storage destination folder for endoscopic images while confirming a folder in the memory card 11 which stores the endoscopic images at a time of inspection, and operating the operation section 5 if necessary.

FIG. 2 is a block diagram for explaining an internal configuration of the main body section of the endoscope apparatus, and an internal configuration of the main body section of the personal computer.

The main body section 2 includes a central processing apparatus (hereinafter, called a CPU) 21, a ROM 22 and a RAM 23, which are connected to one another through a bus 24. Further, a plurality of kinds of interfaces (hereinafter, called I/Fs) 25 to 30 are connected to the bus 24. The I/F 25 is a drive and receiving circuit for performing transmission of a drive signal to an image pickup unit 41 of the scope 3, and reception of an image pickup signal from the image pickup unit 41. The I/F 26 is a drive circuit for transmitting a drive signal to an LED 42 as an illumination section.

The I/F 27 is a circuit for receiving various operation signals from the operation section 5. Various operation signals from the operation section 5 include an operation signal of the joystick 5a. In the case of the configuration in which the touch panel 32 is provided at the LCD 4, the I/F 28 is provided as a circuit for receiving a drive signal to the touch panel 32 and an operation signal from the touch panel 32. The I/F 29 is a circuit for supplying an image signal to the LCD 4.

The I/F 30 is a circuit for performing write of an image signal to the memory card 11 and read of an image signal from the memory card 11. The I/F 30 is electrically connected to the memory card 11 via a connector 33 provided at the main body section 2. The memory card 11 is detachably fitted to the connector 33.

The main body section 2 contains a battery 34 in an inside thereof, and the battery 34 supplies power to various circuits in the main body section 2.

The I/Fs 25 to 30 operate under control of the CPU 21. When the endoscope apparatus 1 is actuated, the CPU 21 outputs various drive signals to the image pickup unit 41 via the I/F 25, and the image pickup unit 41 outputs an image pickup signal to the CPU 21. The CPU 21 outputs a drive instruction signal for the LED 42 to the I/F 26, and the LED 42 is driven by the output of the I/F 26, and illuminates the object, as a result of which, a live image which is an endoscope video relating to the object, is displayed on the LCD 4.

Since the operation section 5 is connected to the CPU 21 via the I/F 27, the operation section 5 supplies, to the CPU 21, various operation signals indicating operation contents by the user to the operation section 5. When the user depresses the freeze button of the operation section 5, the CPU 21 generates a still image based on the image pickup signal from the image pickup unit 41, and when the user further depresses the REC button of the operation section 5, image data of the still image is stored in the memory card 11. Since the still image by freeze is displayed on the LCD 4, the user can confirm the still image, and when the user stores the still image, the user depresses the REC button.

Meanwhile, the PC 101 has the main body section 61, an input apparatus group 71 which is configured by including a keyboard and (or) a pointing device or the like which can input various instructions relating to operations of the main body section 61, and a display apparatus 72 which is configured by a monitor or the like which can display an image or the like corresponding to an image signal outputted from the main body section 61.

Further, the main body section 61 is configured by having a CPU 62 which performs various kinds of computing processing, control and the like relating to operations of the PC 101, a storage device 63 in which various data including programs, software and the like which are executed by the CPU 62 are stored, and a RAM 64 which can temporarily store processing results and the like of the CPU 62. Further, respective units of the CPU 62, the storage device 63 and the RAM 64 are connected to one another through a bus 65. A plurality of various I/Fs 66 to 68 are connected to the bus 65.

The I/F 66 is configured as a circuit which can receive an operation signal relating to the instruction which is performed in the input apparatus group 71. The I/F 67 is configured as a circuit which can generate an image signal for displaying an image or the like on a screen of the display apparatus 72 and can output the image signal, based on the control of the CPU 62. The I/F 68 is configured as a circuit which can perform write of an image signal to the memory card 11, and read of the image signal from the memory card 11. Further, the I/F 68 is electrically connected to the memory card 11 via a connector 69 provided at the main body section 61. The memory card 11 is detachably fitted to the connector 69.

That is to say, according to the configuration described above, the user can confirm the image data which is read from the memory card 11 on the screen of the display apparatus 72 by fitting the memory card 11 in which the image data of an inspection target is accumulated to the main body section 61 and actuating software for image browsing or the like, for example.

Meanwhile, a user can create an optional folder in the memory card 11. For example, the user creates a plurality of folders having a hierarchical structure in the memory card 11 by using a PC before endoscope inspection. More specifically, the user can create a plurality of folders of desired folder names under "root", and can cause each of the folders to store endoscopic images. Further, folders can be further created under the upper folders. That is to say, the user can create the folders having a hierarchical structure in the storage medium. Subsequently, the user can store, in a desired folder, the endoscopic image which is picked up and obtained by the image pickup unit 41 of the scope 3.

Figure 3:
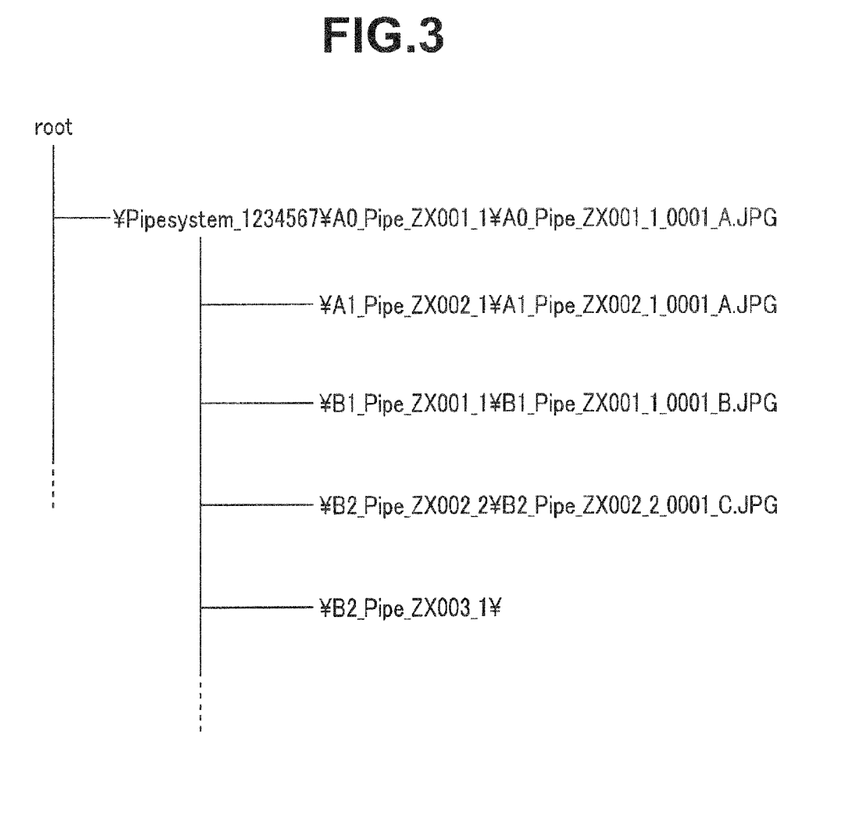
FIG. 3 is a diagram for explaining an example of a folder of a hierarchical structure.

FIG. 3 is a diagram for explaining an example of folders of a hierarchical structure. FIG. 3 schematically expresses respective folders and files included in the folders in order to explain the folders of a hierarchical structure, and here, FIG. 3 shows an example of folders having two hierarchical layers, that is, two levels.

As shown in FIG. 3, the folder of "Pipesystem_1234567" is created at a lower level than "root". Further, at a lower level than the folder of "Pipesystem_1234567", five folders that are "A0_Pipe_ZX001_1", "A1_Pipe_ZX002_1", "B1_Pipe_ZX001_1", "B2_Pipe_ZX002_2", and "B2_Pipe_ZX003_1" are created.

A character string of "Pipesystem_1234567" in a folder name at the lower level than "root" includes, for example, information which makes a piping system of an inspection target identifiable.

Further, character strings of "A0_Pipe", "A1_Pipe", "B1_Pipe" and "B2_Pipe" in folder names at the lower level than "Pipesystem_1234567" include information which makes pipes different from one another and included in the piping system of the inspection target identifiable, for example.

Further, character strings of "ZX001_1", "ZX002_1", "ZX002_2" and "ZX003_1" in folder names at the lower level than the "Pipisystem 1234567" include information which makes inspection purposes for pipes distinguishable, for example.

That is to say, the user creates a folder with an optional name under "root" in the memory card 11. The user may perform folder creating work with an outside apparatus such as the PC 101, or may perform the folder creating work by connecting a hardware keyboard to the endoscope apparatus 1 and operating the hardware keyboard. Further, the user may perform the folder creating work by operating a setting screen displayed on the LCD 4 and a software keyboard which is configured as GUI. Furthermore, in the case of the configuration in which the touch panel 32 is provided on the LCD 4, the user may perform the folder creating work by operating the touch panel 32 or the like, by using the setting screen displayed on the LCD 4. As will be described later, the user can select an optional folder from a plurality of folders which are created like this as a storage destination folder for endoscopic images, and store the obtained endoscopic images in the selected folder.

In the present embodiment, a number of the folder hierarchical layers is two, but the number of the folder hierarchical layers is not limited to two, and may be three or more. Further, as shown by the dotted lines in FIG. 3, a number of folders of the same hierarchical layer may be three or more.

Meanwhile, as shown in FIG. 3, one image file of the endoscopic image in a JPEG format is stored in each of four folders of "A0_Pipe_ZX001_1", "A1_Pipe_ZX002_1", "B1_Pipe_ZX001_1", and "B2_Pipe_ZX002_2". Further, as shown in FIG. 3, an image file of an endoscopic image is not stored in a folder of "B2_Pipe_ZX003_1".

Further, as shown in FIG. 3, the image file of the endoscopic image is given a file name in which, for example, the folder name with the image file stored, a serial number given in sequence according to a timing at which the image file is stored, and a file mark which is given as will be described later are respectively connected with symbols "_" (under bars). That is to say, each of the file names of the endoscopic image illustrated in FIG. 3 is given so as to have regularity of "folder name_serial number_file_mark.JPG".

More specifically, the folder name of "A0_Pipe_ZX001_1", the serial number "0001", and the file mark "A" are respectively connected with the symbols "_" (under bars), and thereby, a file name of "A0_Pipe_ZX001_1_001_A.JPG" is given. The symbol which separates the folder name or the like is not limited to the under bar, but, for example, "-" (hyphen) and a space may be used.

That is to say, according to the image file of the endoscopic image to which the file name is given with regularity as described above, the inspection purpose at a time of acquisition of the image file can be identified based on the file name.

Figure 4:
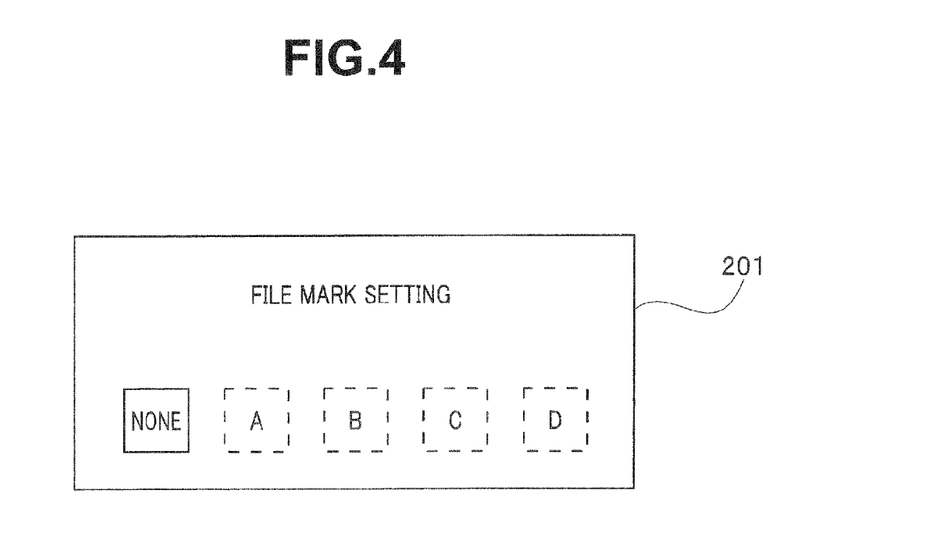
FIG. 4 is a diagram showing a display example of a file mark setting window in setting processing of a file mark.

Here, a file mark which is used when a file name is given will be described. FIG. 4 is a view showing a display example of a file mark setting window in setting processing of a file mark.

A window 201 of FIG. 4 is pop-up displayed on the screen of the LCD 4 in response to the operation input for freeze from the operation section 5 when a still image is displayed.

Subsequently, the user can select any one of four kinds (five kinds if "None" indicating that nothing is added is included) included in the window 201 by performing an operation of the operation section 5.

In the case as illustrated in FIG. 4, one file mark selected from four file marks of "A", "B", "C" and "D" can be added to a file name of a file of a still image. Further, in the respective file marks, "A" corresponds to "No problem (Accept)", "B" corresponds to "Replacement required (Reject)", "C" corresponds to "Repair required (Repair)", and "D" corresponds to "Re-inspection required (Re-Inspect)".

The file mark which is given to the file name of the file of a still image is not limited to a single character, but may be a character string which includes a plurality of characters such as "ACCEPT" and "REPAIR".

Immediately after the window 201 is pop-up displayed, "None" which indicates that no file mark is added is in a selected state as illustrated in FIG. 4. Accordingly, if an operation relating to an instruction to finalize the selection of the file mark is performed in the state illustrated in FIG. 4, a file name which does not include a file mark, like "A0_Pipe_ZX001_1_0001.JPG", for example, is given.

As described above, a file mark is the one that the user optionally gives to show what image the stored image is. For example, in order to classify images into kinds of "No problem (Accept)", "Replacement required (Reject)", "repair required (Repair)", and "Re-inspection required (Re-Inspect)", a file mark is added to the file names. That is to say, a file mark is inspection result information which the user who is an inspector gives to an endoscopic image by looking at the endoscopic image. Further, there is a kind "None". "None" means no file mark (that is, a file mark cannot be given). Accordingly, addition of a file mark is according to a user's option.

Subsequently, processing or the like which is performed when the user browses the endoscopic image group stored in the memory card 11 by using the PC 101 will be described. In the following description, for simplification, the description will be continued while the case of each of the folders in the memory card 11 being created to have the hierarchical structure as in FIG. 3 is properly cited as an example.

First, the user performs an instruction to actuate predetermined image browsing software (image viewer) which is stored in the storage device 63 by operating the input apparatus group 71, in a state in which the memory card 11 is fitted to the connector 69 of the PC 101.

Meanwhile, based on the operation signal received via the I/F 66, the CPU 62 of the PC 101 reads the predetermined image browsing software from the storage device 63 and actuates the predetermined image browsing software, and performs processing for displaying the endoscopic image group stored in the memory card 11 on the display apparatus 72 according to a predetermined display mode.

More specifically, the CPU 62 performs the processing for displaying the endoscopic image group (image file group) which is stored in one folder which is selected by the operation of the input apparatus group 71, for example, on the display apparatus 72 without including an endoscopic image group (image file group) which is stored in folders at the lower level than the one folder, as the processing relating to the aforementioned predetermined display mode, based on the operation signal received via the I/F 66. According to such processing, when the folder of "A0_Pipe_ZX001_1" is selected, for example, in the case of each of the folders in the memory card 11 having the hierarchical structure as in FIG. 3, only the image of "A0_Pipe_ZX001_1_0001_A.JPG" is displayed on the display apparatus 72.

According to the present embodiment, as the aforementioned predetermined display mode, an optional display mode other than a list display mode which will be described later can be applied.

Thereafter, the user performs an instruction to switch the display mode of the endoscopic image group stored in the memory card 11 from the aforementioned predetermined display mode to the list display mode which will be described later, by operating the input apparatus group 71.

Figure 5:
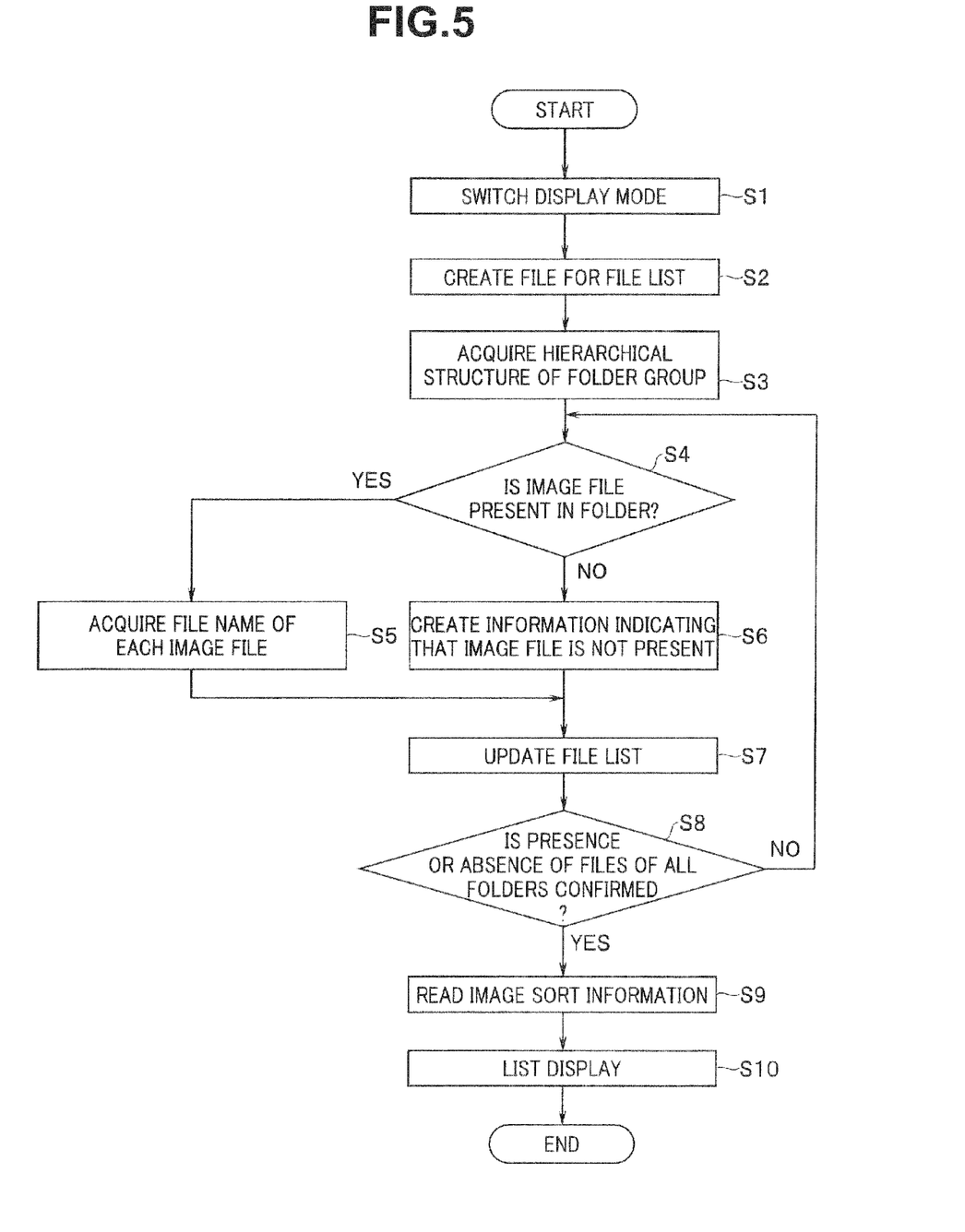
FIG. 5 is a flowchart showing an example of processing of a case in which a list display mode is selected.

Here, specific processing or the like which is performed when the list display mode is selected will be described with reference to a flowchart of FIG. 5. FIG. 5 is a flowchart showing an example of processing in a case of the list display mode being selected.

In the present embodiment, a state is cited as an example, in which a folder to be an origin for list display of image files is selected based on the operation signal received via the I/F 66 before the flowchart of FIG. 5 is executed. The selected folder to be the origin will be described as a selected folder hereinafter. In the example, "Pipesystem_1234567" which is the lower folder of "root" in the memory card 11 is the selected folder.

First, when the CPU 62 detects that the instruction to switch the display mode from the aforementioned predetermined display mode to the list display mode is performed, based on the operation signal received via the I/F 66 (step S1 of FIG. 5), the CPU 62 creates a file (in a text format, for example) for use in description of a file list which makes a location of each file stored in the selected folder individually (by full path) identifiable (step S2 of FIG. 5). In the file list, not only the location of each file, but also a status flag which shows a state of presence or absence of an image in each folder is preferably described. Further, in the example, the file list is created as an individual file, but may be retained as data on a region of the RAM 64.

Next, the CPU 62 acquires hierarchical structure information of the selected folder (step S3 of FIG. 5). More specifically, immediately after the processing of step S2 of FIG. 5 is performed, for example, the CPU 62 acquires the hierarchical structure information indicating that "A0_Pipe_ZX001_1", "A1_Pipe_ZX002_1", "B1_Pipe_ZX001_1", "B2_Pipe_ZX002_2", and "B2_Pipe_ZX003_1" are included as the lower folder of "Pipesystem_1234567" of FIG. 3.

The CPU 62 detects whether or not an image file is present in each of the folders belonging to the hierarchical structure in the hierarchical structure which is acquired by the processing of step S3 of FIG. 5, and the selected folder has (step S4 of FIG. 5).

When the CPU 62 obtains a detection result that an image file is present in each of the folders by the processing of step S4 of FIG. 5, the CPU 62 acquires a file name of each of the image files in the folders in which the image files are present (step S5 of FIG. 5). By performing such processing, the CPU 62 acquires the file name of "A0_Pipe_ZX001_1_0001_A.JPG" which is present in the folder of "A0_Pipe_ZX001_1", for example.

Further, when the CPU 62 obtains a detection result that an image file is not present in each of the folders by the processing of step S4 of FIG. 5, the CPU 62 generates information showing the detection result (step S6 of FIG. 5).

When the CPU 62 obtains the detection result that an image file is not present in the folder of "B2_pipe_ZX003_1", for example, the CPU 62 stores a status flag indicating that an image file is not present in the folder of "B2_Pipe_ZX003_1" on the RAM 64 as the information indicating the detection result.

The CPU 62 may generate a dummy image file for showing the detection result and store the dummy image file in the folder of "B2_Pipe_ZX003_1", instead of storing the status flag on the RAM 64. The dummy image file is given a file name substantially including the aforementioned regularity as the file name which makes the folder name of the storage destination of the dummy image file identifiable, but as to the file mark, "A" is indiscriminately given to the dummy image files. Accordingly, when the CPU 62 obtains the detection result that an image file is not present in the folder of "B2_Pipe_ZX003_1", for example, the CPU 62 generates a dummy image file given a file name of "B2_Pipe_ZX003_1_0001_A.JPG" as the dummy image file including image data which is the information indicating the detection result. At this time, the dummy image file is stored in the folder of "B2_Pipe_ZX003_1", but, for example, the CPU 62 may create a folder for storing the dummy image file inside (or outside) the selected folder, and may store the dummy image file in the folder. A file name of the dummy image file is made by the same rule as the above description based on the original folder name for which the presence or absence of the image file is determined For example, when the CPU 62 obtains a detection result that an image file is not present in the folder of "B2_Pipe_ZX003_1", the CPU 62 generates a dummy image file given the file name of "B2_Pipe_ZX003_1_0001_A.JPG" as the dummy image file including the image data showing the information indicating the detection result. Subsequently, the CPU 62 stores the dummy image file in the folder inside (or outside) the aforementioned selected folder.

Thereafter, the CPU 62 updates the file list in accordance with the processing result of S5 or S6 of FIG. 5 (step S7 of FIG. 5).

More specifically, the CPU 62 updates the file list by acquiring the file name of the image file of "A0_Pipe_ZX001_1_0001_A.JPG" by the processing of step S5 of FIG. 5, and adding "root¥Pipesystem_1234567¥A0_Pipe_ZX001_1çA0_Pipe_ZX001_1_0001_A.JPG" which is a full path of the image file to the file list. The CPU 62 may further add the status flag indicating that the image file was present to the file list.

Meanwhile, for example, when the status flag indicating that an image file is not present in "B2_Pipe_ZX003_1" is stored on the RAM 64 by the processing of step S6 of FIG. 5, the CPU 62 updates the file list by adding "root¥Pipesystem_1234567¥B2_Pipe_ZX003_1" which is a full path of the folder to the file list and also adding the status flag indicating that an image file is not present.

Further, an example of a case without use of a status flag will be described. The CPU 62 updates the file list by acquiring the image file name "A0_Pipe_ZX001_1_0001_A.JPG" by the processing of step S5 of FIG. 5, for example, and adding "root¥Pipesystem_1234567¥A0_Pipe_ZX001_1¥A0_Pipe_ZX001_1_0001_A.JPG" which is a full path of the image file to the file list. Meanwhile, when the CPU 62 generates the dummy image file "B2_Pipe_ZX003_1_0001_A.JPG" by the processing of step S6 of FIG. 5, for example, the CPU 62 updates the file list by adding "root¥Pipesystem_1234567¥B2_Pipe_ZX003_1¥B2_Pipe_ZX003_1_0001_A.JPG" which is a full path of the dummy image file to the file list.

The CPU 62 performs determination of whether or not presence or absence of image files (acquire the presence information of image files) with respect to all the folders (including the subfolders and the lower folders of the selected folder) which belong to the selected folder by the processing of step S7 of FIG. 5 (step S8 of FIG. 5).

Subsequently, when the CPU 62 obtains a determination result that the presence or absence of image files is not confirmed with respect to all the folders which belong to the selected folder by the processing of step S8 of FIG. 5, the CPU 62 returns to step S4 of FIG. 5 and performs the processing.

Further, when the CPU 62 obtains a determination result that the presence or absence of the image files is confirmed with respect to all the folders which belong to the selected folder based on the hierarchical structure information of the selected folder which is acquired in step S3, by the processing of step S8 of FIG. 5, the CPU 62 completes creation of the file list, and successively performs processing of step S9 of FIG. 5 which will be described later.

That is to say, the CPU 62 creates the file list which makes the location of the folder storing the image file individually (by full path) identifiable in each of the folders which belong to the selected folder, by repeating the processing from step S4 to step S8 of FIG. 5.

After the CPU 62 completes creation of the file list, the CPU 62 determines the display sequence at the time of list display of each of the image files described in the file list by reading image sort information from the storage device 63 or the RAM 64 (step S9 of FIG. 5).

Here, the aforementioned image sort information is assumed to be initially set so that display is performed in the ascending sequence of the file names, for example. Further, in the aforementioned image sort information, setting is made rewritable so that display is in a desired display sequence of the user, by an operation of the input apparatus group 71. More specifically, the user can rewrite the setting of the image sort information so that display is performed in an ascending sequence or a descending sequence based on at least any one of, for example, the file name, the file mark, the inspection purpose, the status flag and a comment embedded in the image file. As information which is written as the aforementioned comment, for example, an apparatus name which is used in the inspection, a cause of abnormality, details of the inspection result and the like are conceivable.

Subsequently, the CPU 62 performs processing for list-displaying each of the image files described in the file list in the display apparatus 72 in the display sequence which is determined by the processing of step S9 of FIG. 5 (step S10 of FIG. 5).

Figure 6:
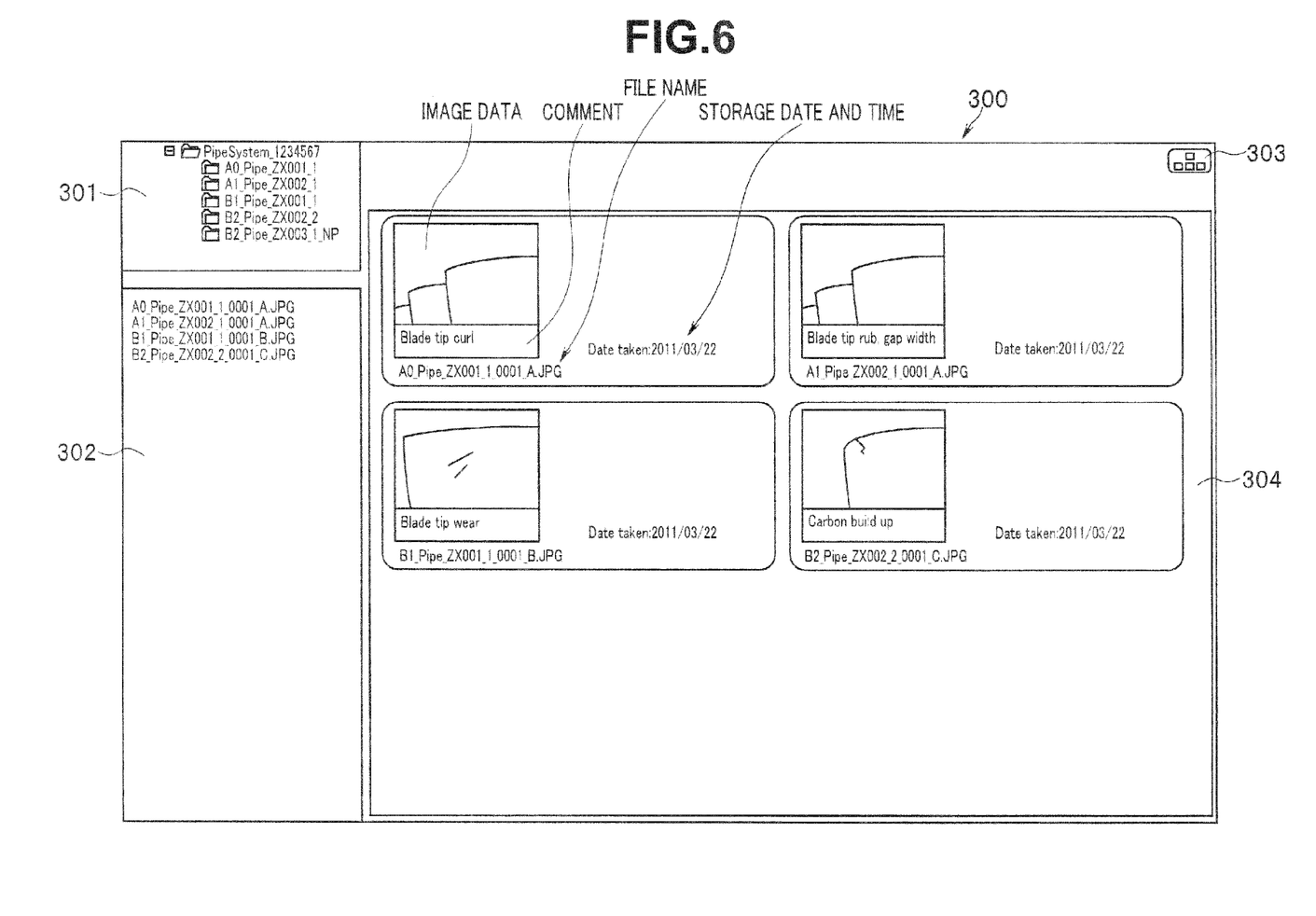
FIG. 6 is a view showing one example of a screen which is displayed when the list display mode is selected.

More specifically, the CPU 62 performs processing for displaying a list display screen 300 which includes a display mode as shown in FIG. 6, for example, in the display apparatus 72 in step S10 of FIG. 5. FIG. 6 is a view showing one example of a screen which is displayed when the list display mode is selected.

The list display screen 300 of FIG. 6 includes a folder selection region 301 in which the folder (selected folder) to be the origin of the list display can be selected from the respective folders which are present in the memory card 11, an image list display region 302 in which the file name of each of the image files which are list-displayed is displayed in a list, a display switch button 303 which is capable of selecting any one of the aforementioned predetermined display mode and the list display mode and switching to the selected mode, and an image display region 304 capable of list-displaying the image files and information relating to the image files.

That is to say, according to the list display screen 300 like this, the user can select one folder to be the origin of list display in the list display mode from the respective folders displayed in the folder selection region 301, by operating the input apparatus group 71.

Further, according to the list display screen 300 like this, the user can switch the display mode of the image file in the image display region 304 by selecting any one of the aforementioned predetermined display mode and the list display mode, by operating the display switch button 303 by using the input apparatus group 71.

When the CPU 62 detects that the folder of "Pipesystem_1234567" is selected from the respective folders displayed in the folder selection region 301, and the list display mode is selected with the display switch button 303, based on the operation signals received via the I/F 66, based on the file list generated by the aforementioned processing, the CPU 62 displays "A0_Pipe_ZX001_1_0001_A.JPG", "A1_Pipe_ZX002_1_0001_A.JPG", "B1_Pipe_ZX001_1_0001_B.JPG" and "B2_Pipe_ZX002_2_0001_C.JPG" which are the character strings indicating the file names of the respective image files which are present in the respective lower folders which belong to "Pipesystem_1234567" on the image list display region 302 (see FIG. 6). At this time, when the CPU 62 displays the folder name (for example, "B2_Pipe_ZX003_1") in which an image file is not present in the folder selection region 301, the CPU 62 preferably displays the folder name like "B2_Pipe_ZX003_1_NP" by adding the information indicating that an image is not present such as "No_Photograph" ("NP") to the folder name, for example.

Next, the CPU 62 list-displays the image data which the image files have, comments embedded in the image files, storage dates and times (photographing dates and times) of the image files, and the file names of the image files, in the image display region 304 in a distinguishable state for each image file (for example, with a display region assigned to each image file), based on the file list generated by the aforementioned processing and the display sequence determined by the aforementioned processing (see FIG. 6).

Thereby, the user notices that information indicating that an image file is not present in the folder is added to the folder name of "B2_Pipe_ZX003_1_NP" in the folder selection region 301, and can easily recognize that the image file is not present in the folder of "B2_Pipe_ZX003_1_NP".

Figure 7:
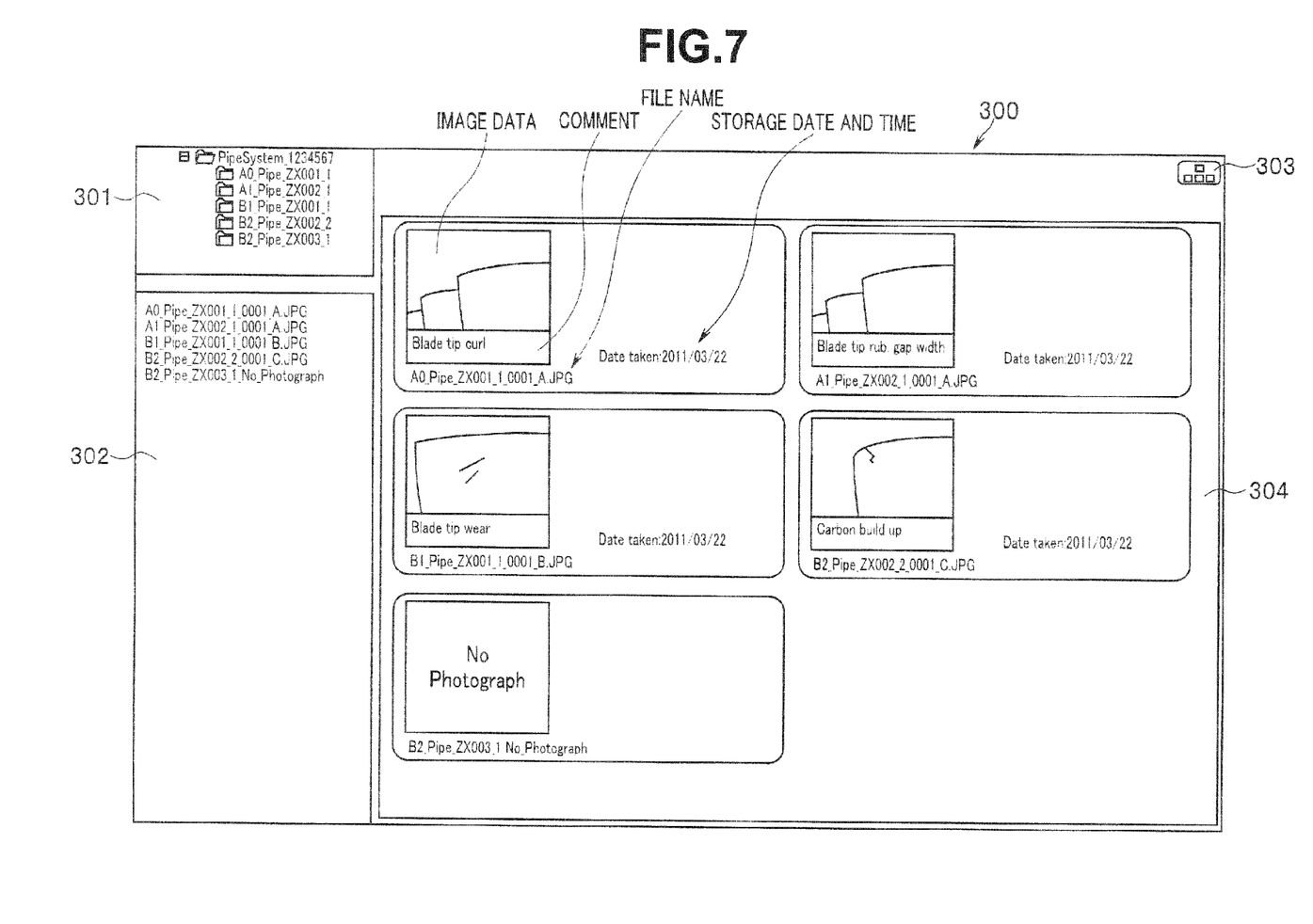
FIG. 7 is a view showing one example of the screen which is displayed when the list display mode is selected.

Further, as shown in FIG. 7, the file name may be displayed with the information indicating that an image file is not present being added to the file name, in the image list display region 302. In the image list display region 302, the character string of "No_Photograph" which is the information indicating that an image file is not present is added to the folder name of "B2_Pipe_ZX003_1" in which an image file is not present, and the folder name is displayed. Meanwhile, in the image display region 304, the aforementioned folder name of "B2_Pipe_ZX003_1" in which an image file is not present, and the character string of "No_Photograph" which is the information indicating that an image file is not present are displayed, and image data indicating that no image file which is similar to the image data which the dummy image file has is present in the folder is displayed. At this time, the image data is the image data as a template which is prepared in advance, and the file name based on each of the folder names does not have to be added as the dummy image file.

Figure 8:
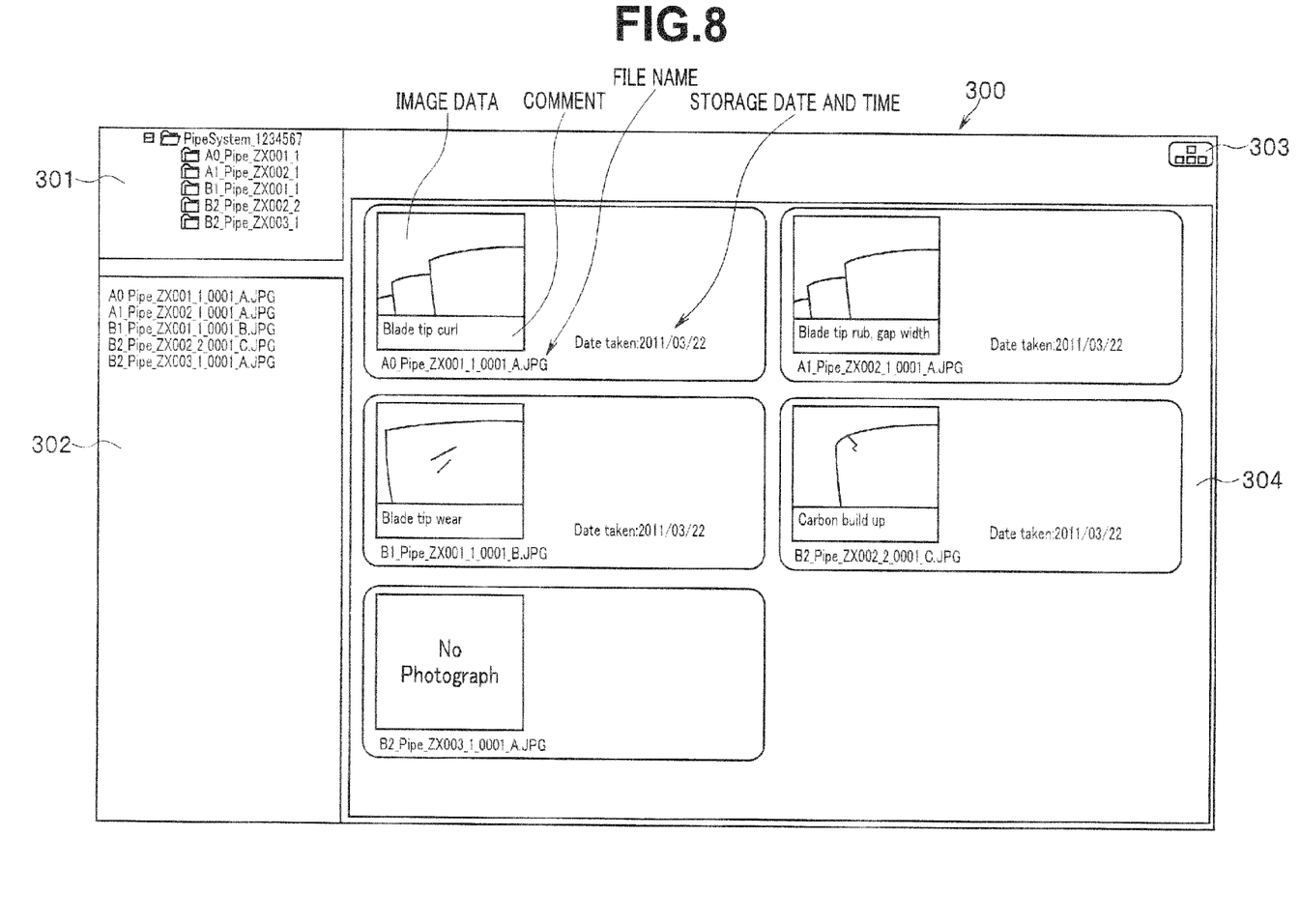
FIG. 8 is a view showing one example of the screen which is displayed when the list display mode is selected.

FIG. 8 is a display example of a case in which absence of an image file in the "B2_Pipe_ZX003_1" folder is detected in the processing of step S6 of FIG. 5, and the dummy image file having the file name of "B2_Pipe_ZX003_1_0001_A.JPG" is created. The CPU 62 displays "A0_Pipe_ZX001_1_0001_A.JPG", "A1_Pipe_ZX002_1_0001_A.JPG" , "B1_Pipe_ZX001_1_0001_B.JPG", "B2_Pipe_ZX002_2_0001_C.JPG", and "B2_Pipe_ZX003_1_0001_A.JPG" which are the character strings showing the file names of the respective image files which are present in the respective lower folders which belong to "Pipesystem_1234567" in the image list display region 302, based on the file list generated by the aforementioned processing.

In the dummy image file, storage date and time, and a comment are not present. Accordingly, in the display region which is assigned to the image file of "B2_Pipe_ZX003_1_0001_A.JPG", the file name of the image file, and the image data including the character string of "No Photograph" are displayed (see FIG. 8). Thereby, the user notices that the file name including the folder name of "B2_Pipe_ZX003_1" and the image data including the character string of "No Photograph" are displayed together in the image display region 304, and can easily recognize that an image file is not present in the folder of "B2_Pipe_ZX003_1".

As long as absence of an image file in one folder can be visually recognized, information including another display mode except for the file name and image data (including the character string of "No Photograph (NP)" as described above may be displayed in the list display screen 300.

According to the list display screen 300 including the display mode as in FIG. 6, information which makes presence or absence of an image file identifiable for each lower folder with the folder of "Pipesystem_1234567" as the origin is displayed in the folder selection region 301 and the image display region 304. Accordingly, the user can easily confirm presence or absence of the image file in each of the folders without performing a conventional complicated operation of, for example, sequentially opening the respective lower folders of the folder of "Pipesystem_1234567" one by one.

Figure 9:
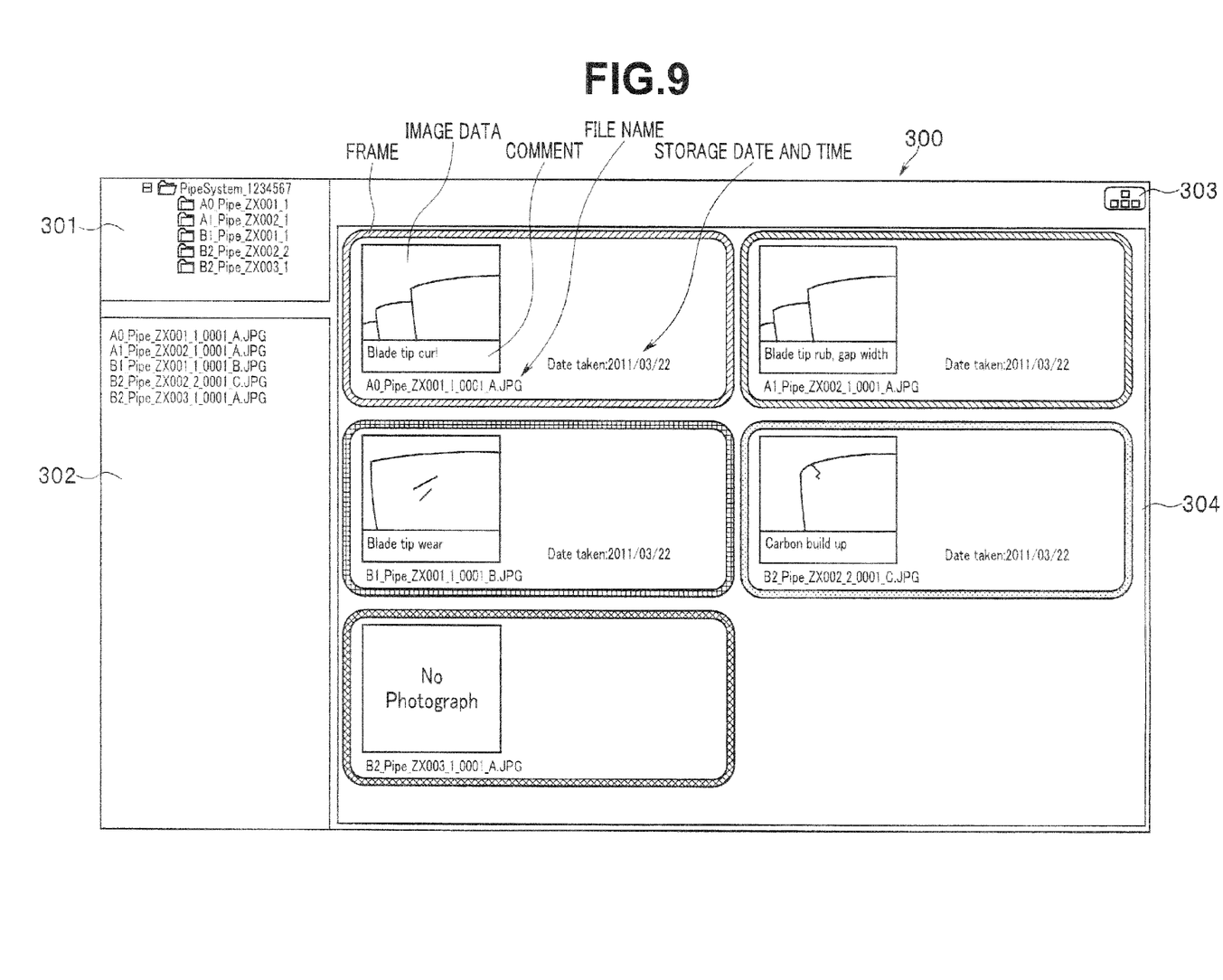
FIG. 9 is a view showing one example of the screen which is displayed when the list display mode is selected.

For example as shown in FIG. 9, the list display screen 300 of the present embodiment may be a screen in which a frame generated to have a different color and (or) pattern for each folder is added to the display region assigned to each image file in the image display region 304, as an identifier which is visually identifiable as belonging to the same or a different folder.

Figure 10:
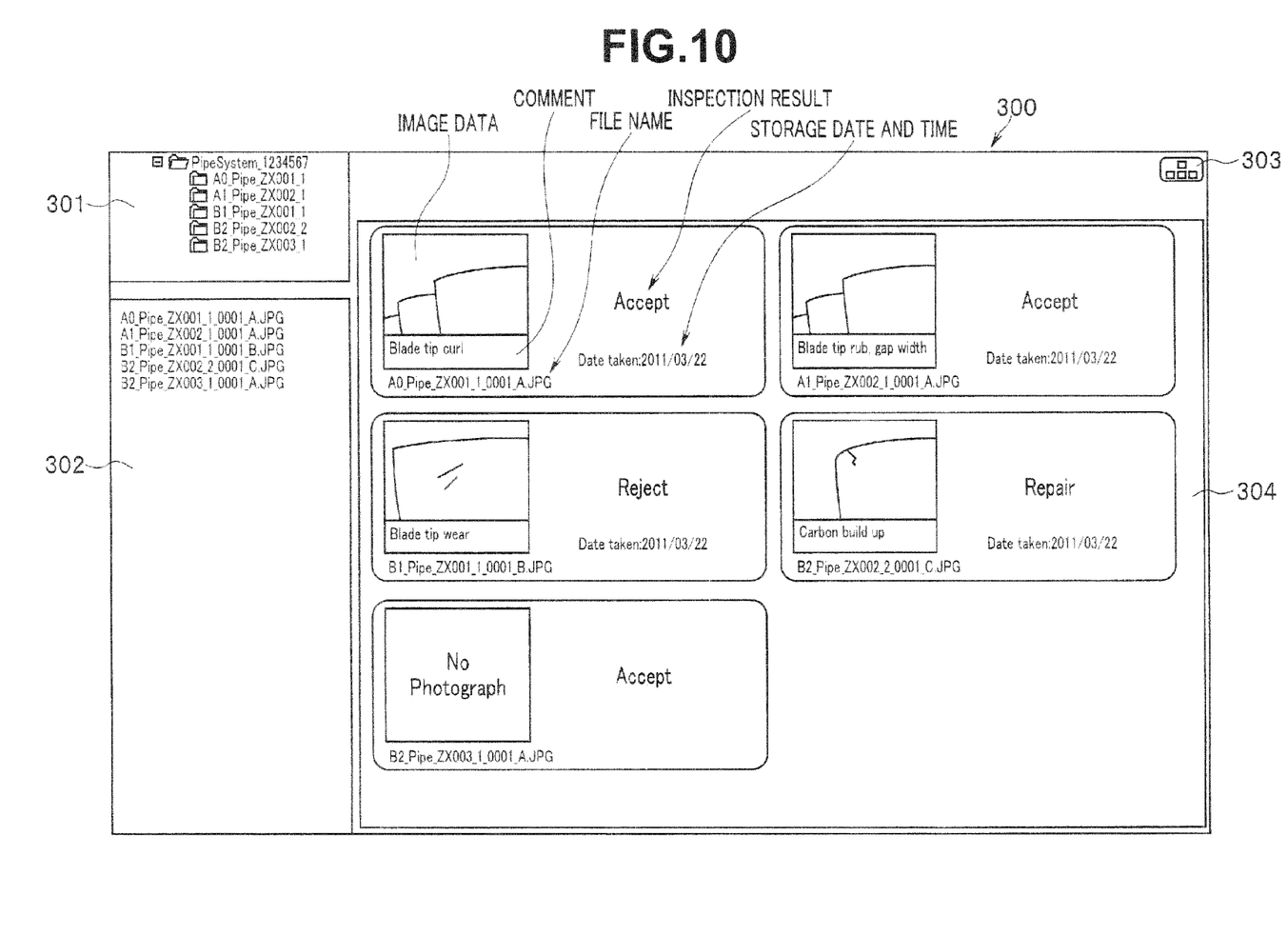
FIG. 10 is a view showing one example of the screen which is displayed when the list display mode is selected.

Further, the list display screen 300 of the present embodiment may be a screen in which the information of the inspection result corresponding to the file mark added to the file name is displayed in the display region which is assigned to each image file in the image display region 304, as shown in FIG. 10, for example. More specifically, for example, when the file mark "A" is added to the file name, the character string of "Accept" may be displayed, and when the file mark "B" is added to the file name, the character string of "Reject" may be displayed. When the file mark "C" is added to the file name, the character string of "Repair" may be displayed, and when the file mark "D" is added to the file name, the character string of "Re-Inspect" may be displayed. Meanwhile, for example, when a file mark which shows whether or not the image file is the image file that can be used for measurement such as stereo measurement is added to the file name, a character string indicating that measurement is possible or measurement is impossible may be displayed in accordance with the file mark.

Figure 11:
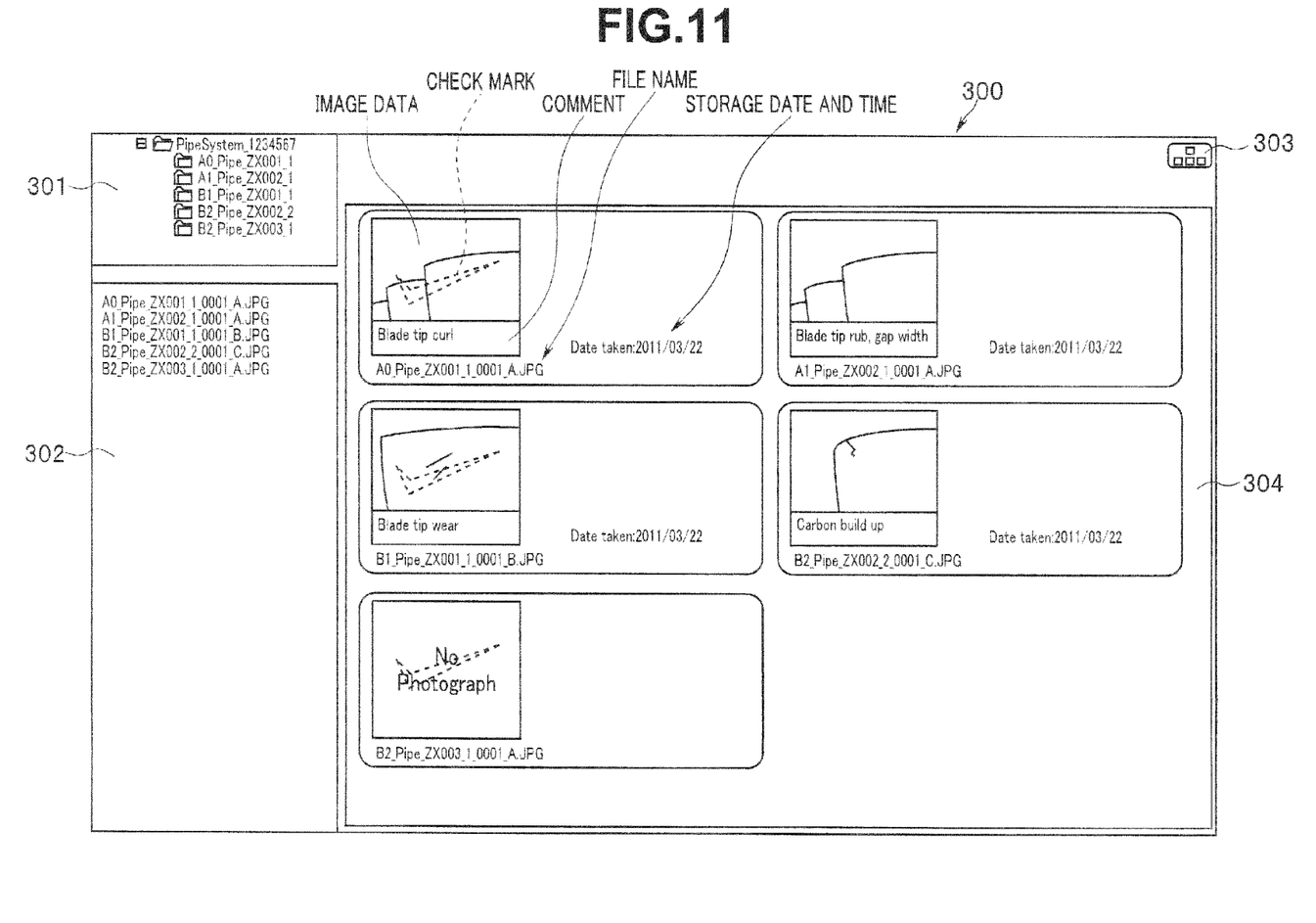
FIG. 11 is a view showing one example of the screen which is displayed when the list display mode is selected.

Further, the list display screen 300 of the present embodiment may be made so that a checkmark can be individually added to a desired image file of the user among the respective image files which are list-displayed in the image display region 304, as shown in FIG. 11, for example. According to such a configuration, the image file to which the aforementioned checkmark is added can be selectively used when a report following a predetermined template is automatically created, for example. More specifically, when checkmarks are added as shown in FIG. 11, for example, three image files of "A0_Pipe_ZX001_1_0001_A.JPG", "B1_Pipe_ZX001_1_0001_B.JPG", and "B2_Pipe_ZX003_1_0001_A.JPG" are selectively used when the report following the predetermined template is automatically created.

Figure 12:
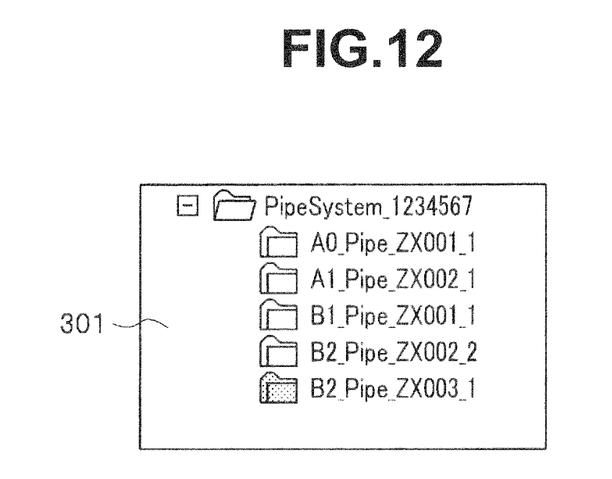
FIG. 12 is a view showing one example of a display mode for making a folder in which an image file is not present identifiable.

Further, according to the present embodiment, as shown in FIG. 12, for example, in the folder selection region 301, to an icon of the folder in which an image file is not present, a display mode differing from an icons of other folders, for example, a color and (or) a pattern may be added, and the folder may be displayed.

Figure 13:
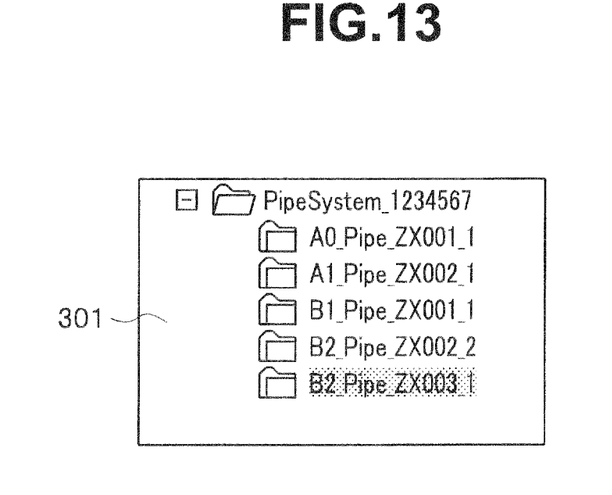
FIG. 13 is a view showing one example of the display mode for making a folder in which an image file is not present identifiable.

Further, according to the present embodiment, as shown in FIG. 13, for example, in the folder selection region 301, a character string corresponding to a folder in which an image file is not present may be displayed by being emphasized.

The embodiment which is described above is not limited to an embodiment that is applied to an image file of endoscopic images which are acquired by inspection using an endoscope apparatus, and can be widely applied to image files of inspection images which are acquired by inspection using other inspection apparatuses such as a nondestructive inspection apparatus, for example.

Furthermore, all or part of a program code of software which executes processing or the like for displaying the list display screen of the embodiment described above is recorded or stored in movable media such as a flexible disk and a CD-ROM, storage devices such as a ROM and a hard disk of an endoscope main body, and the like. The program code is read by a computer, and all or part of the operation is executed. Alternatively, all or part of the program can be distributed or provided via a communication network. A user can easily realize the inspection image display apparatus and method of the present invention by downloading the program via the communication network and installing the program in a computer, or installing the program in the computer from a storage medium.

The present invention is not limited to the aforementioned embodiment, and various changes and applications can be made within a range without departing from a gist of the invention.

What is claimed is:

1. An endoscopic inspection image display control apparatus comprising a CPU which is configured to operate as:
a display switch section configured to switch a display mode at a time of displaying a plurality of endoscopic inspection images stored in a storage device in which a plurality of image folders arranged in a hierarchical structure are created by selecting the display mode from one of a predetermined display mode and a list display mode;
an image folder selecting section configured to select one image folder to be an origin of list display from the plurality of image folders when the list display mode is selected by the display switch section; and a control section that performs display control such that (i) an image folder selection region for displaying the plurality of image folders from which the one image folder is selected by the image folder selecting section, and (ii) an image display region for displaying each endoscopic inspection image stored in each image folder belonging to an image folder group with the one image folder as the origin, are simultaneously displayed in a first display area and a second display area, respectively, wherein among the plurality of image folders displayed in the image folder selection region, (i) with respect to an image folder in which a file of an endoscopic inspection image is present, the control section performs further control to display image data showing the endoscopic inspection image which is present in the image folder to be displayed in the image display region, and (ii) with respect to an image folder in which an endoscopic inspection image is not present, the control section performs further control such that information indicating that the endoscopic inspection image is not present is displayed in one of the image display region and the image folder selection region.

2. The endoscopic inspection image display control apparatus according to claim 1, wherein the CPU is further configured to operate as:

an image folder information acquiring section that acquires information relating to presence or absence of the file of the endoscopic inspection image in the plurality of image folders in the storage device, wherein the control section generates a predetermined image indicating the image folder in which the file of the endoscopic inspection image is not present, and causes a file of the predetermined image to be stored in each image folder in which the file of the endoscopic inspection image is not present according to the information which is acquired by the image folder information acquiring section.

3. The endoscopic inspection image display control apparatus according to claim 2, wherein a file name which makes an image folder name of a storage destination individually identifiable is added to each file of the predetermined image.

4. The endoscopic image inspection image display control apparatus according to claim 1, wherein the CPU is further configured to operate as:

an image folder information acquiring section that acquires information relating to presence or absence of the file of the endoscopic inspection image in the plurality of image folders in the storage device, wherein the control section generates a predetermined image indicating the image folder in which the file of the endoscopic inspection image is not present, and causes a file of the predetermined image to be stored in a predetermined image folder different from each image folder in which the file of the endoscopic inspection image is not present according to the information which is acquired by the image folder information acquiring section.

5. The endoscopic inspection image display control apparatus according to claim 2, wherein the control section performs further control to display the predetermined image in the image display region as the information indicating that the endoscopic inspection image is not present in the image folder.

6. The endoscopic inspection image display control apparatus according to claim 5, wherein the control section performs further control such that a file mark added to the file of the endoscopic inspection image is displayed in the image display region together with the image data showing the endoscopic inspection image present in the image folder, and such that a file mark added to the file of the predetermined image is displayed in the image display region together with the predetermined image.

7. The endoscopic inspection image display control apparatus according to claim 1, wherein among the image folders displayed in the image folder selection region, with respect to the image folder in which the file of the endoscopic inspection image is not present, the control section performs further control such that a folder name of the image folder displayed in the image folder selection region is displayed, with characters indicating that the endoscopic inspection image is not present in the image folder being added to the folder name as the information indicating that the endoscopic inspection image is not present in the image folder.

8. The endoscopic inspection image display control apparatus according to claim 1, wherein among the image folders displayed in the image folder selection region, with respect to the image folder in which the file of the endoscopic inspection image is not present, the control section performs further control such that image data indicating that the endoscopic inspection image is not present in the image folder is displayed in the image display region.

9. The endoscopic inspection image display control apparatus according to claim 1, wherein among the image folders displayed in the image folder selection region, with respect to the image folder in which the file of the endoscopic inspection image is not present, the control section performs further control such that an icon of the image folder is displayed in a display mode different from a display mode of icons of other image folders.

10. The endoscopic inspection image display control apparatus according to claim 1, wherein among the image folders displayed in the image folder selection region, with respect to the image folder in which the file of the endoscopic inspection image is not present, the control section performs further control such that a folder name of the image folder displayed in the image folder selection region is displayed by being emphasized.

11. An endoscopic inspection image display control method comprising:

switching a display mode at a time of displaying, on a display, a plurality of endoscopic inspection images stored in a storage device in which a plurality of image folders arranged in a hierarchical structure are created, by selecting the display mode from one of a predetermined display mode and a list display mode;

selecting one image folder to be an origin of list display from the plurality of image folders when the list display mode is selected by the switching; and performing display control of the display such that (i) an image folder selection region for displaying the plurality of image folders from which the one image folder is selected by the selecting, and (ii) an image display region for displaying each endoscopic inspection image stored in each image folder belonging to an image folder group with the one image folder as the origin, are simultaneously displayed in a first display area and a second display area, respectively, wherein among the plurality of image folders displayed in the image folder selection region, (i) with respect to an image folder in which a file of an endoscopic inspection image is present, the display control further displays image data showing the endoscopic inspection image which is present in the image folder to be displayed in the image display region, and (ii) with respect to an image folder in which an endoscopic inspection image is not present, the display control further displays information indicating that the endoscopic inspection image is not present in one of the image display region and in the image folder selection region.

12. The endoscopic inspection image display control method according to claim 11, further comprising:
acquiring information relating to presence or absence of the file of the endoscopic inspection image in the plurality of image folders in the storage device,
wherein the display control further generates a predetermined image indicating the image folder in which the file of the endoscopic inspection image is not present, and causes a file of the predetermined image to be stored in each image folder in which the file of the endoscopic inspection image is not present according to the acquired information.

13. The endoscopic inspection image display control method according to claim 12, wherein a file name which makes an image folder name of a storage destination individually identifiable is added to each file of the predetermined image.

14. The endoscopic inspection image display control method according to claim 11, further comprising,
acquiring information relating to presence or absence of the file of the endoscopic inspection image in the plurality of image folders in the storage device,
wherein the display control further generates a predetermined image indicating the image folder in which the file of the endoscopic inspection image is not present, and causes a file of the predetermined image to be stored in a predetermined image folder different from each image folder in which the file of the endoscopic inspection image is not present according to the acquired information.

15. The endoscopic inspection image display control method according to claim 12, wherein the display control further causes the predetermined image to be displayed in the image display region as the information indicating that the endoscopic inspection image is not present in the image folder.

16. The endoscopic inspection image display control method according to claim 15, wherein the display control further displays a file mark added to the file of the endoscopic inspection image in the image display region together with the image data showing the endoscopic inspection image present in the image folder, and displays a file mark added to the file of the predetermined image in the image display region together with the predetermined image.

17. The endoscopic inspection image display control method according to claim 11, wherein among the image folders displayed in the image folder selection region, with respect to the image folder in which the file of the endoscopic inspection image is not present, the display control further causes a folder name of the image folder displayed in the image folder selection region to be displayed, with characters indicating that the endoscopic inspection image is not present in the image folder being added to the folder name as the information indicating that the endoscopic inspection image is not present in the image folder.

18. The endoscopic inspection image display control method according to claim 11, wherein among the image folders displayed in the image folder selection region, with respect to the image folder in which the file of the endoscopic inspection image is not present, the display control further causes image data indicating that the endoscopic inspection image is not present in the image folder to be displayed in the image display region.

19. The endoscopic inspection image display control method according to claim 11, wherein among the image folders displayed in the image folder selection region, with respect to the image folder in which the file of the endoscopic inspection image is not present, the display control further causes an icon of the image folder to be displayed in a display mode different from a display mode of icons of other image folders.

20. The endoscopic inspection image display control method according to claim 11, wherein among the image folders displayed in the image folder selection region, with respect to the image folder in which the file of the endoscopic inspection image is not present, the display control further causes a folder name of the image folder displayed in the image folder selection region to be displayed by being emphasized.

* * * * *